United States Patent [19]
Barbul et al.

[11] Patent Number: 5,733,884
[45] Date of Patent: Mar. 31, 1998

[54] ENTERAL FORMULATION DESIGNED FOR OPTIMIZED WOUND HEALING

[75] Inventors: Adrian Barbul, Baltimore, Md.; Lisa Stewart Bebenek, Glencoe, Ill.; David A. Mark, Oak Park, Ill.; Susan Trimbo, Evanston, Ill.; Diana Twyman, Chicago, Ill.; Paul Lin, Fullerton, Calif.

[73] Assignee: Nestec Ltd., Vevey, Switzerland

[21] Appl. No.: 554,475

[22] Filed: Nov. 7, 1995

[51] Int. Cl.⁶ .............................. A61K 38/00; A23J 1/00; A23G 3/00

[52] U.S. Cl. .................. 514/21; 514/2; 514/23; 514/54; 514/558; 514/560; 514/565; 514/943; 426/72; 426/607; 426/656; 426/658; 424/439

[58] Field of Search ..................... 514/21.2, 23, 54, 514/558, 560, 565, 943; 426/72, 607, 656, 658; 424/439

[56] References Cited

U.S. PATENT DOCUMENTS

| | | |
|---|---|---|
| Re. 28,093 | 7/1974 | Balassal . |
| Re. 29,909 | 2/1979 | Kurtz . |
| 2,912,359 | 11/1959 | Anigstein et al. . |
| 3,003,917 | 10/1961 | Beiler et al. . |
| 3,400,199 | 9/1968 | Balassa . |
| 3,476,855 | 11/1969 | Balassa . |
| 3,478,146 | 11/1969 | Balassa . |
| 3,558,771 | 1/1971 | Balassa . |
| 3,624,201 | 11/1971 | Balassa . |
| 3,632,754 | 1/1972 | Balassa . |
| 3,804,949 | 4/1974 | Balassa . |
| 3,903,268 | 9/1975 | Balassa . |
| 3,904,753 | 9/1975 | Yamasaki et al. . |
| 3,911,116 | 10/1975 | Balassa . |
| 3,914,413 | 10/1975 | Balassa . |
| 4,001,396 | 1/1977 | Feuer . |
| 4,049,802 | 9/1977 | Fox . |
| 4,056,520 | 11/1977 | Sonenberg et al. . |
| 4,094,973 | 6/1978 | Robertson . |
| 4,177,261 | 12/1979 | Dietze et al. . |
| 4,265,233 | 5/1981 | Sugitachi et al. . |
| 4,287,184 | 9/1981 | Young . |
| 4,318,906 | 3/1982 | Llopart . |
| 4,330,527 | 5/1982 | Arima et al. . |
| 4,399,123 | 8/1983 | Grant et al. . |
| 4,401,651 | 8/1983 | Knutson . |
| 4,414,202 | 11/1983 | Silvetti . |
| 4,414,976 | 11/1983 | Linnau et al. . |
| 4,423,036 | 12/1983 | Schneider . |
| 4,426,378 | 1/1984 | Holaday . |
| 4,427,654 | 1/1984 | Austin . |
| 4,431,582 | 2/1984 | Stenn . |
| 4,442,655 | 4/1984 | Stroetmann . |
| 4,443,437 | 4/1984 | Marshall et al. . |
| 4,444,760 | 4/1984 | Thomas . |
| 4,447,418 | 5/1984 | Maddoux . |
| 4,485,098 | 11/1984 | Ishikawa et al. . |
| 4,503,037 | 3/1985 | Raskai . |
| 4,507,285 | 3/1985 | Kuhne . |
| 4,532,134 | 7/1985 | Malette et al. . |
| 4,575,457 | 3/1986 | Maxarin . |
| 4,604,283 | 8/1986 | Gresham . |
| 4,617,326 | 10/1986 | Bjornberg et al. . |
| 4,657,758 | 4/1987 | Berger et al. . |
| 4,666,708 | 5/1987 | Berger et al. . |
| 4,698,301 | 10/1987 | Hill et al. . |
| 4,699,788 | 10/1987 | Catsimpoolas et al. . |

(List continued on next page.)

FOREIGN PATENT DOCUMENTS

| | | |
|---|---|---|
| 8289452 | 4/1983 | Australia . |
| 48473 | 3/1982 | European Pat. Off. . |
| 61917 | 10/1982 | European Pat. Off. . |
| 78191 | 5/1983 | European Pat. Off. . |
| 90997 | 10/1983 | European Pat. Off. . |
| 150053 | 7/1985 | European Pat. Off. . |
| 165492 | 12/1985 | European Pat. Off. . |
| 199331 | 10/1986 | European Pat. Off. . |
| 201741 | 11/1986 | European Pat. Off. . |
| 225109 | 6/1987 | European Pat. Off. . |
| 2316197 | 8/1987 | European Pat. Off. . |
| 324227 | 7/1989 | European Pat. Off. . |

(List continued on next page.)

OTHER PUBLICATIONS

Barbul et al, *Surgery*, vol. 108, No. 2, pp. 331–337, 1990.

Berthold et al, *Metabolism*, vol. 44, No. 4, pp. 466–473, Apr. 1995.

Albina et al, *Arginine metabolism in wounds*, Am.J. Physiol., pp. E459–E467 (1988).

Albina et al, *Temporal Expression of Different Pathways in l-Arginine Metabolism in Healing Wounds*, The Journal of Immunobiology, vol. 144, No. 10, pp. 3877–3880 (1990).

Barbul et al, *Arginine enhances wound healing and lymphocyte immune responses in humans*, Surgery, vol. 108, pp. 331–336 (1990).

Berthold et al, *Isotopic Evidence for the Differential Regulation of Arginine and Proline Synthesis in Man*, Metabolism, vol. 44, No. 4, pp. 466–473 (1995).

(List continued on next page.)

*Primary Examiner*—Cecilia J. Tsang
*Assistant Examiner*—Abdel A. Mohamed
*Attorney, Agent, or Firm*—Hill, Steadman & Simpson

[57] ABSTRACT

The present invention provides an enteral nutritional formulation that meets the nutrient requirements of patients with wounds. The present invention meets the unique nutrient needs of the acute or chronic patient that are generated due to tissue repair and healing requirements of wounds. To this end, in an embodiment, the present invention provides a method for providing nutritional support to a patient with an acute or chronic wound comprising the step of administering a therapeutically effective amount of composition comprising a protein source including an arginine source and a proline source in the ratio by weight of approximately 1:0.5 to about 4:1. The composition may also include a carbohydrate source, a lipid source including an appropriate n6:n3 ratio, and at least the U.S. RDA for vitamins and minerals provided in an amount of formula supplying 1000 kcal, with vitamin A, beta-carotene, vitamin C, vitamin E, thiamine, pyridoxine, biotin and zinc being supplied in amounts above the U.S. RDAs.

20 Claims, No Drawings

U.S. PATENT DOCUMENTS

| | | |
|---|---|---|
| 4,701,325 | 10/1987 | Funakoshi et al. . |
| 4,708,873 | 11/1987 | Schulte . |
| 4,708,948 | 11/1987 | Fryling et al. . |
| 4,725,438 | 2/1988 | Lezer . |
| 4,732,758 | 3/1988 | Hurion et al. . |
| 4,760,051 | 7/1988 | Pickart . |
| 4,767,746 | 8/1988 | Catsimpoolas et al. . |
| 4,772,591 | 9/1988 | Meisner . |
| 4,778,679 | 10/1988 | Silvetti . |
| 4,808,402 | 2/1989 | Leibovich et al. . |
| 4,837,017 | 6/1989 | Leveen et al. . |
| 4,837,019 | 6/1989 | Georgalas et al. . |
| 4,837,024 | 6/1989 | Michaeli . |
| 4,844,898 | 7/1989 | Komori et al. . |
| 4,847,083 | 7/1989 | Clark . |
| 4,883,664 | 11/1989 | Sharkey . |
| 4,889,844 | 12/1989 | Silvetti et al. . |
| 4,892,516 | 1/1990 | Harle . |
| 4,898,734 | 2/1990 | Edeman et al. . |
| 4,900,673 | 2/1990 | Harper et al. . |
| 4,917,889 | 4/1990 | Carty . |
| 4,917,890 | 4/1990 | McAnalley . |
| 4,929,577 | 5/1990 | Cornell . |
| 4,931,430 | 6/1990 | Sudilovsky et al. . |
| 4,937,230 | 6/1990 | Pickart . |
| 4,937,323 | 6/1990 | Dunn et al. . |
| 4,942,031 | 7/1990 | Levin . |
| 4,944,948 | 7/1990 | Fielding et al. . |
| 4,950,483 | 8/1990 | Ksander et al. . |
| 4,950,699 | 8/1990 | Holman . |
| 4,956,354 | 9/1990 | Gutierrez . |
| 4,957,742 | 9/1990 | Knighton . |
| 4,960,594 | 10/1990 | Honeycutt . |
| 4,970,298 | 11/1990 | Berg et al. . |
| 4,973,466 | 11/1990 | Reich . |
| 4,975,421 | 12/1990 | Browder et al. . |
| 4,980,403 | 12/1990 | Bateman et al. . |
| 4,983,581 | 1/1991 | Antoniades et al. . |
| 4,990,339 | 2/1991 | Bunnelle et al. . |
| 5,000,746 | 3/1991 | Meiss . |
| 5,023,090 | 6/1991 | Levin . |
| 5,024,841 | 6/1991 | Chu et al. . |
| 5,035,887 | 7/1991 | Antoniades et al. . |
| 5,047,249 | 9/1991 | Band et al. . |
| 5,049,553 | 9/1991 | Sudilovsky . |
| 5,053,387 | 10/1991 | Alexander ................................. 514/2 |
| 5,059,425 | 10/1991 | Furcht et al. . |
| 5,064,652 | 11/1991 | Bay . |
| 5,073,378 | 12/1991 | Magdassi et al. . |
| 5,081,106 | 1/1992 | Bentley et al. . |
| 5,084,281 | 1/1992 | Dillon . |
| 5,091,176 | 2/1992 | Braatz et al. . |
| 5,110,604 | 5/1992 | Chu et al. . |
| 5,112,608 | 5/1992 | Berg et al. . |
| 5,124,155 | 6/1992 | Reich . |
| 5,128,136 | 7/1992 | Bentley et al. . |
| 5,130,124 | 7/1992 | Garelick et al. . |
| 5,132,119 | 7/1992 | Lee . |
| 5,134,229 | 7/1992 | Kamp et al. . |
| 5,137,734 | 8/1992 | Castellot et al. . |
| 5,141,928 | 8/1992 | Goldman . |
| 5,145,676 | 9/1992 | Cerami et al. . |
| 5,145,681 | 9/1992 | Durham et al. . |
| 5,155,038 | 10/1992 | Eyal et al. . |
| 5,156,847 | 10/1992 | Lewis et al. . |
| 5,160,483 | 11/1992 | Kang et al. . |
| 5,165,938 | 11/1992 | Knighton . |
| 5,166,132 | 11/1992 | Gordon . |
| 5,166,331 | 11/1992 | della Valle . |
| 5,177,065 | 1/1993 | Silvetti et al. . |
| 5,178,883 | 1/1993 | Knighton . |
| 5,192,536 | 3/1993 | Huprich . |
| 5,196,196 | 3/1993 | Berg et al. . |
| 5,198,225 | 3/1993 | Bonte et al. . |
| 5,202,118 | 4/1993 | Gillis et al. . |
| 5,219,576 | 6/1993 | Chu et al. . |
| 5,221,668 | 6/1993 | Henningfield et al. ................... 514/23 |
| 5,234,914 | 8/1993 | Gallina . |
| 5,246,708 | 9/1993 | von Borstel et al. . |
| 5,254,538 | 10/1993 | Holick et al. . |
| 5,260,071 | 11/1993 | Lemelson . |
| 5,268,180 | 12/1993 | Morancais et al. . |
| 5,271,939 | 12/1993 | Kunkle et al. . |
| 5,271,943 | 12/1993 | Bogart et al. . |
| 5,391,550 | 2/1995 | Carriglia et al. ......................... 514/23 |
| 5,436,228 | 7/1995 | Postlethwait et al. .................... 514/12 |
| 5,576,351 | 11/1996 | Yoshimura et al. ...................... 514/565 |
| 5,578,576 | 11/1996 | Ceddlin ................................... 514/21 |

FOREIGN PATENT DOCUMENTS

| | | |
|---|---|---|
| 1767900 | 9/1971 | Germany . |
| 2507223 | 9/1976 | Germany . |
| 2916711 | 11/1980 | Germany . |
| 2945239 | 5/1981 | Germany . |
| 3026368 | 2/1982 | Germany . |
| 3124981 | 1/1983 | Germany . |
| 234230 | 3/1986 | Germany . |
| 3618407 | 12/1987 | Germany . |
| 3820817 | 12/1988 | Germany . |
| 289543 | 5/1991 | Germany . |
| 50-046656 | 4/1975 | Japan . |
| 56-133213 | 10/1981 | Japan . |
| 59-137422 | 8/1984 | Japan . |
| 61-027982 | 2/1986 | Japan . |
| 63-033361 | 2/1988 | Japan . |
| 8603974 | 7/1986 | WIPO . |
| 8607263 | 12/1986 | WIPO . |
| 8704925 | 8/1987 | WIPO . |
| 8801166 | 2/1988 | WIPO . |
| 8807076 | 9/1988 | WIPO . |
| 8809604 | 12/1988 | WIPO . |
| 8809606 | 12/1988 | WIPO . |
| 8901780 | 3/1989 | WIPO . |
| 8901781 | 3/1989 | WIPO . |
| 8903688 | 5/1989 | WIPO . |
| 9102716 | 3/1991 | WIPO . |
| 9109524 | 7/1991 | WIPO . |

OTHER PUBLICATIONS

Chernoff et al, *The Effect of a Very High–Protein Liquid Formula (Replete®) on Decubitus Ulcer Healing in Long–Term Tube–Fed Institutionalized Patients*, Clintec Nutrition Company, Brochure (1991).

Clintec Nutrition Company, Video Study Guide, *Nutritional Aspects of Wound Healing* (1994).

Clintec Nutrition Company, *Replete®* Brochure (1993).

Gardiner et al, *The Role of the Imino Transporter Protein in Sepsis–Impaired Intestinal Proline Absorption*, Journal of Parenteral and Enteral Nutrition, vol. 17, pp. 507–512 (1993).

Hiramatsu et al, *Plasma proline and leucine kinetics: response to 4 wk with proline–free diets in young adults*, Am J Clin Nutr, vol. 60, pp. 207–215 (1994).

Jaksic et al, *Proline metabolism in adult male burned patients and healthy control subjects*, Am J Clin Nutr, vol. 54, pp. 408–413 (1991).

Kirk et al, *Arginine stimulates wound healing and immune function in elderly human beings*, Surgery, vol. 114, pp. 155–160 (1993).

Kirk et al, *Role of Arginine in Trauma, Sepsis, and Immunity*, Journal of Parenteral and Enteral Nutrition, vol. 14, No. 5, Supplement, pp. 226S–229S (1990).

Wagner, *Nutritional Management of the Pressure Ulcer Patient*, Clintec Nutrition Company, Brochure (1990).

Wakabayashi et al, *Arginine but not proline changes to be essential amino acid in the rat with massive resection of the small intestine*, P.102, p. 84.

Wakabayashi et al, *Arginine Becomes an Essential Amino Acid after Massive Resection of Rat Small Intestine*, The Journal of Biological Chemistry, No. 23, pp. 32667–32671 (1994).

Filipec et al, *Topical cyclosporine and corneal wound healing*, Cornea, vol. 11, pp. 546–552 (1992).

Hartmann et al, *Effect of tissue perfusion and oxygenation on accumulation of collagen in healing wounds. Randomized study in patients after major abdominal operations*, Eur J Surg, vol. 158, pp. 521–526 (1992).

Nakagawa et al, *Inactivation of substance P by granulation tissue–derived gelatinase*, Biochem Pharmacol, vol. 44, pp. 1773–1777 (1992).

Seiki et al, *Effect of Z–103 on wound healing by dermal incision in guinea pigs*, Nippon Yakurigaku Zasshi, vol. 100, pp. 165–172 (1992).

Suh et al, *Insulin–like growth factor–I reverses the impairment of wound healing induced by cortiocosteroids in rats*, Endocrinology, vol. 131, pp. 2399–2403 (1992).

Salomatin et al, *Effect of alpha–acidic glycoprotein on oxyproline metabolism in experimental thermal trauma*, Vopr Med Khim, vol. 38, pp. 58–60 (1992).

Irie et al, *Histological and biochemical analysis of the fibrous tissue induced by implantation of synthetic ligament (Dacron): an experimental study in a rat model*, J Orthop Res, vol. 10, pp. 866–894 (1992).

Graf et al, *Influence of 5–fluorouracil and folinic acid on colonic healing: an experimental study in the rat*, Br J Surg, vol. 79, pp. 825–828 (1992).

Nishimura, *Role of testosterone propionate and insulin in the regeneration and growth of bone*, Meikai Daigaku Shigaku Zasshi, vol. 19, pp. 291–309 (1990).

Pfeffer, *Progressive ventricular dilation in experimental myocardial infarction and its attenuation by angiotensin–converting enzyme inhibition*, Am J Cardiol, vol. 68, pp. 17D–25D (1991).

Hogstrom et al, *Tension leads to increased neutrophil accumulation and decreased laparotomy sound strength*, Surgery, vol. 107, pp. 215–219 (1990).

Sofianos et al, *The effect of hypovolaemia on healing of the right and the left colon. An experimental study*, S Afr J Surg, vol. 30 (1992).

Chiego, *An Ultrasound and autoradiographic analysis of primary and replacement odontoblasts following cavity preparation and wound healing in the rat molar*, Proc Finn Dent Soc, vol. 88, Suppl 1, pp. 243–256 (1992).

Aita et al, *Studies on the healing promoting action of Z–103 in chronic gastric ulcer models of rats*, Nippon Yakurigaku Zassi, vol. 99, pp. 345–352 (1992).

Yoshida et al, *Basal studies on the model of circular excisional wounds made on the dorsal skin of rats treated with hydrocortisone*, Nippon Yakurigaku Zasshi, vol. 98, pp. 369–377 (1991).

de Roy et al, *Cytostatics and anastomotic healing in the intestine: an experimental study on the effect of parenteral nutrition*, Eur Surg Res, vol. 24, pp. 103–111 (1992).

Mizuno et al, *Effects of oral administration of various non–steroidal anti–inflammatory drugs on bone growth and bone wound healing in mice*, Meikai Daigaku Shigaku Zasshi, vol. 19, pp. 234–250 (1990).

Tadros et al, *Blood transfusion impairs the healing of experimental intestinal anastomoses*, Ann Surg, vol. 215, pp. 276–281, (1992).

Jugdutt et al, *Effect of long–term captopril therapy on left ventricular remodeling and function during healing of canine myocardial infarction*, J Am Coll Cardiol, vol. 19, pp. 713–721 (1992).

Saclarides et al, *Fibrin glue improves the healing of irradiated bowel anastomoses*, Dis Colon Rectum, vol. 35, pp. 249–252 (1992).

Guan, *Significance of determination of serum and urinary hydroxyproline in healthy subjects and patients with hyperplastic scars*, Chung Hua Cheng Hsing Shang Wai Ko Tsa Chih, vol. 7, pp. 174–176 (1991).

Seyer–Hansen et al, *The Influence of aminoguanidine on borohydride reducible collagen cross–links and wound strength*, Connect Tissue Res, vol. 26, pp. 181–186 (1991).

Renvall, *Bone cement and wound healing, An Experimental study in the rat*, Ann Chir Gynaecol, vol. 80, pp. 285–288 (1991).

Boon et al, *A comparative analysis of healing of surgical cleft lip corrected in utero and neonates*, Plast Reconstr Surg, vol. 89, pp. 11–17 (1992).

Kozlov et al, *Comparative characteristics of oxyproline excretion in urine in children with post–burn hypertrophic and keloid scars*, Vopr Med Khim, vol. 37, pp. 17–19 (1991).

Abrahamsson, *Matrix metabolism and healing in the flexor tendon. Experimental studies on rabbit tendon*, Scand J Plast Reconstr Surg Hand Surg Suppl, vol. 23, pp. 1–51 (1991).

Garrel et al, *Chronic administration of growth hormone–releasing factor increases wound strength and collagen maturation in granulation tissue*, J Surg Res, vol. 51, pp. 297–302 (1991).

Johnson et al, *Effect of allopurinol on adriamycin–induced impairment of wound healing*, J Invest Surg, vol. 4, pp. 323–331 (1991).

Johnson et al, *Preliminary study of the protective effect of the calcium channel blocker, nifedipine, on adriamycin–induced tissue injury*, J Invest Surg, vol. 4, pp. 313–322 (1991).

Fumagalli et al, *Effects of intraperitoneal chemotherapy on anastomotic healing in the rat*, J Surg Res, vol. 50, pp. 82–87 (1991).

Hennessey et al, *EGF increases short–term type I collagen accumulation during wound healing in diabetic rats*, J Pediatr Surg, vol. 25, pp. 893–897 (1990).

Houston et al, *Tissue plasminogen activator reverses the deleterious effect of infection on colonic wound healing*, Ann Surg, vol. 211, pp. 130–135 (1990).

Madison et al, *Effects of a proprietary topical medication on wound healing and collagen deposition in horses*, Am J Vet Res, vol. 52, pp. 459–472 (1991).

Laato, *The effect of nonspecific immune stimulation on wound healing*, Prog Clin Biol Res, vol. 365, pp. 459–472 (1991).

Adzick et al, *Scarless wound healing in the fetus; the role of the extracellular matrix*, Prog Clin Biol Res, vol. 365, pp. 177–192 (1991).

Kiyohara et al, *Improvement in wound healing by epidermal growth factor (EGF) ointment, II. Effect of protease inhibitor, nafamostat, on stabilization and efficacy of EGF in burn,* J Pharmacobiodyn, vol. 14, pp. 47–52 (1991).

Orita et al, *Kinetic analysis of experimental post–operative peritoneal healing; the incorporation of proline and glycocyamine by exudative and tissue repair cells,* Jpn J Surg, vol. 31, pp. 322–328 (1991).

de Roy et al, *Intraperitoneal Cytostatics impair healing of experimental intestinal anastomoses,* Br J Cancer, vol. 63, pp. 937–941 (1991).

de Sousa et al, *Effects of ciclofenac sodium on intestinal anastomotic healing. Experimental study on the small intestine of rabbits,* Dis Colon Rectum, vol. 34, pp. 613–617 (1991).

Mastboom et al, *Intestinal anastomotic healing in the absence of suture material: an experimental study in rats,* Int J Colorectal Dis, vol. 6, pp. 33–37 (1991).

Katakami et al, *Keratocyte activity in wound healing after epikeratophakia in rabbits,* Invest Ophthalmol Vis Sci, vol. 32, pp. 1837–1845 (1991).

Iannotti et al, *Synthesis and characterization of magnetically responsive albumin microspheres containing cis–hydroxyproline for scar inhibition,* J Orthop Res, vol. 9, pp. 432–444 (1991).

Kang et al, *Thrombin stimulation of synthesis and secretion of fibronectin by human A549 epithelial cells and mouse LB fibroblasts,* J Histochem Cytochem, vol. 39, pp. 413–423 (1991).

Mastboom et al, *Influence of methylprednisolone on the healing of intestinal anastomoses in rats,* Br J Surg, vol. 78, pp. 54–56 (1991).

van der Ham et al, *Effect of fibrin sealant on the healing colonic anastomosis in the rat,* Br J Surg, vol. 78, pp. 49–53 (1991).

Frankle et al, *The effects of testosterone propionate and methenolone enanthate on the healing of humeral osteotomies in the Wistar rat,* J Invest Surg, vol. 3, pp. 93–113 (1990).

Gelberman et al, *Healing of digital flexor tendons: importance of the interval from injury to repair. A biomechanical, biochemical and morphological study in dogs,* J Bone Joint Surg [AM}, vol. 73, pp. 66–75 (1991).

Agren et al, *Influence of zinc deficiency on breaking strength of 3–week–old skin incisions in the rat,* Acta Chir Scand, vol. 156, pp. 667–670 (1990).

Bushmelev et al, *Predicting the course of wound healing after appendectomy using the hydroxyproline test,* Khirurgiia (Mosk), vol. 8, pp. 24–27 (1990).

Chowcat et al, *Direct measurement of collagenase in colonic anastomosis,* Br J Surg, vol. 77, pp. 1284–1287 (1990).

Vaxman et al, *Improvement in the healing of colonic anastomoses by vitamin B5 and C supplements. Experimental study in the rabbit,* Ann Chir, vol. 44, pp. 512–520 (1990).

Burd et al, *Foetal wound healing in a large animal model; the deposition of collagen is confirmed,* Br J Plast Surg, vol. 43, pp. 571–577 (1990).

Dempsey et al, *Laser assisted fusion of the rat stomach: preliminary studies,* J Surg Res, vol. 48, pp. 223–229 (1990).

Park et al, *The influence of a histamine 2–receptor antagonist on the healing of an experimentally induced gastric mucosal lesion,* APMIS, vol. 98, pp. 305–312 (1990).

Sabiston et al, *Allograft ligament transplantation. A morphological and biochemical evaluation of a medial collateral ligament complex in a rabbit model,* Am J Sports Med, vol. 18, pp. 160–168 (1990).

Hersh et al, *Topical nonsteroidal agents and corneal wound healing,* Arch Ophthalmol, vol. 108, pp. 577–583 (1990).

Terzioglu et al, *The effect of prostaglandin E1 on colonic anastomotic healing. A comparison study,* Dis Colon Rectum, vol. 33, pp. 44–48 (1990).

Bliss, *Aetiology of pressure sores,* Rev. Clin. Gerontol. (U.K.), vol. 3, pp. 379–397 (1993).

Andreyev et al, *Parenteral nutrition in adult intensive care,* Postgrad. Med. J. (U.K.), vol. 69, pp. 841–845 (1993).

Keenan et al, *How to make sure your older patients are getting enough zinc,* Geriatrics, vol. 48, pp. 57–65 (1993).

Telfer et al, *Drug and nutrient aspects of wound healing,* Dermatol. Clin., vol. 11, pp. 729–737 (1993).

Fullana et al, *Skin prolylhydroxylase activity and wound healing,* Eur. Surg. Res. (Switzerland), vol. 25, pp. 370–375 (1993).

Dudrick et al, *Divergent regulation of fuel utilization in human fibroblasts by epidermal growth factor,* J. Surg. Res., vol. 54, pp. 305–310 (1993).

Bianchetti et al, *Risk factors for the development of pressure sores in hospitalized elderly patients: Results of a prospective study,* Arch. Gerontol. Geriatr. (Netherlands), vol. 16, pp. 225–232 (1993).

Boyce et al, *Nutritional regulation of cultured analogues of human skin,* J. Toxicol. Cutaneous Ocul. Toxicol., vol. 12, pp. 161–171 (1993).

Skaer, *Total parenteral nutrition: Clinical considerations,* Clin. Ther., vol. 15, pp. 272–282 (1993).

Conine et al, *Pressure sore prophylaxis in elderly patients using slab foam or customized contoured foam wheelchair cushions,* Occup. Ther. J. Res., vol. 13, pp. 101–116 (1993).

Nelson et al, *Prevalence of malnutrition in the elderly admitted to long–term–care facilities,* J. Am. Diet. Assoc. vol. 93, pp. 459–461 (1993).

Spoelhof et al, *Pressure ulcers in nursing home patients,* Am. Fam. Phys., vol. 47, pp. 1207–1215 (1993).

Perez, Pressure ulcers: *Updated guidelines for treatment and prevention,* Geriatrics, vol. 48, pp. 39–41; 43–44, (1993).

Bujko et al, *Wound healing after preoperative radiation for sarcoma of soft tissues,* Surg. Gynecol. Obstet., vol. 176, pp. 124–134 (1993).

Konstantinides et al, *The impact of nutrition on wound healing,* Crit Care Nurse, vol. 13, pp. 25–33 (1993).

Derganc, *Present trends in fluid therapy, metabolic care, and prevention of infection in burned children,* Crit Care Med., vol. 21 (9 Suppl), pp. 397–399 (1993).

Rackett et al, *Diet and dermatology, The role of dietary manipulation in the prevention and treatment of cutaneous disorders,* J Am Acad Dermatol, vol. 29, pp. 447–461 (1993).

Bergstrom, *Lack of nutrition in AHCPR prevention guideline, Decubitus,* vol. 6, pp. 4.6 (1993).

Gherini et al, *Delayed wound healing and nutritional deficiencies after total hip arthroplasty,* Clin Orthop, vol. 293, pp. 188–195 (1993).

Callan et al, *Use of bovine–derived hydroxyapatite in the treatment of edentulous ridge defects: a human clinical and histologic case report,* J Periodontal, vol. 64, pp. 572–582 (1993).

Ziemer et al, *Skin changes and pain in the nipple during the 1st week of lactation*, J Obstet Gynecol Neonatal Nurs, vol. 22, pp. 247–256 (1993).

Subrahmanyam, *Honey impregnated gauze versus polyurethane film (OpSite) in the treatment of burns—a prospective randomized study*, Br J Plast Surg, vol. 46, pp. 322–323 (1993).

Lowthian, *Acute patient care: pressure areas*, Br J Nurs, vol. 2, pp. 449–450; 452; 454–458 (1993).

Steinleitner et al, *New modalities under development for adhesion prevention: immunomodulatory agents and poloxamer barrier materials*, Prog Clin Biol Res, vol. 381, pp. 235–251 (1993).

Trujillo, *Effects of nutritional status on wound healing*, J Vasc Nurs, vol. 11, pp. 12–18, (1993).

Okamoto et al, *Augmentation of skin flap survival by selective intraarterial infusion of prostaglandin E1: experimental and clinical studies*, Ann Plast Surg, vol. 30, pp. 154–158 (1993).

Osak, *Nutrition and wound healing*, Plast Surg Nurs, vol. 13, pp. 29–36 (1993).

Hodges, *Impact of nutritional care upon return–to–duty rates*, Mil Med, vol. 158, pp. 157–160 (1993).

Porras–Reyes et al, *Enhancement of wound healing by the alkaloid taspine defining mechanism of action*, Proc Soc Exp Biol Med, vol. 203, pp. 18–25 (1993).

Breslow et al, *The Importance of dietary protein in healing pressure ulcers*, J Am Geriatr Soc, vol. 41, pp. 357–362 (1993).

Applebaum, *An hydroxylapatite prosthesis for defects of the incus long process*, Laryngoscope, vol. 103, pp. 330–332 (1993).

Tan et al, *A comparison of Zenoderm with DuoDERM E in the treatment of split skin graft donor sites*, Br J Plast Surg, vol. 46, pp. 82–84 (1993).

Zhou et al, *Effects of chronic spinal cord injury and pressure ulcer on 25(OH–vitamin D levels*, J Am Paraplegia Soc, vol. 16, pp. 9–13 (1993).

Ing et al, *Spinal cord injury and vitamin D metabolism*, J Am Paraplegia Soc, vol. 16, pp. 1–2 (1993).

Kristensen, *Spontaneous healing of traumatic tympanic membrane perforations in man: A century of experience*, J. Laryngol. Otol. (U.K.), vol. 106, pp. 1037–1050, (1992).

Erban et al, *A 130–kDa protein on endothelial cells binds to amino acids 15–42 of the Bbeta chain of fibrinogen*, J. Biol. Chem., vol. 267, pp. 2451–2458 (1992).

Leicester et al, *Vitamin C depletion and pressure sores*, Br. Med. J., vol. 305, p. 1443, (1992).

Verdery, *Malnutrition and chronic inflammation: Causes of effects of frailty?*, Aging (Italy), vol. 4, pp. 262–263, (1992).

Allman et al, *Nutrition in dystrophic epidermolysis bullosa*, Pediatr. Dermatol, vol. 9, pp. 231–238 (1992).

Ter Riet et al, *Health–care professionals' views of the effectiveness of pressure ulcer treatments. A survey among nursing–home physicians, dermatologists and nursing staff in the Netherlands*, Clin Exp. Dermatol. (U.K.), vol. 17, pp. 328–331 (1992).

American Dietetic Association, *Self–assessment questionnaire for RDs*, J. Am. Diet. Assoc., vol. 92, pp. 1117–1118 (1992).

Kerstetter et al, *Malnutrition in the institutionalized older adult*, J. Am. Diet. Assoc., vol. 92, pp. 1109–1116 (1992).

Rockwell et al, *Reversible burn injury*, J. Burn Care Rehabil., vol. 13, pp. 403–406 (1992).

Emanuele et al, *Pressure sores: How to prevent and treat them*, Postgrad. Med., vol. 91, pp. 113–118; 120 (1992).

Raiten, *Nutritional correlates of human immunodeficiency virus infection*, Eur. J. Gastroenterol. Hepatol. (U.K.), vol. 4, pp. 428–442 (1992).

Nezu et al, *Role of zinc in surgical nutrition*, J Nutr Sci Vitaminol (Japan), pp. 530–533 (1992).

Haynes, *Nutrition in the severely head–injured patient*, Clin. Rehabil. (U.K.), vol. 6, pp. 153–158 (1992).

Hill, *Body composition research: Implications for the practice of clinical nutrition*, J. Parenter. Enter. Nutr., vol. 16, pp. 197–218 (1992).

Sasaki, *The effects of basic fibroblast growth factor and doxorubicin on cultured human skin fibroblasts: relevance to wound healing*, J Dermatol (Japan), vol. 19, pp. 664–666 (1992).

Skeie et al, *The role of branched–chain amino acids in nutrition*, Care Crit. Ill, pp. 68–69; 72–73 (1992).

Gerding et al, *Oxyquinoline–containing ointment vs. standard therapy for stage I and stage II skin lesions*, Dermatol Nurs, vol. 4, pp. 389–398 (1992).

Pedersen et al, *Nutrition as a prognostic indicator in amputations. A prospective study of 47 cases*, Acta Orthop Scand (Denmark), vol. 63, pp. 675–678 (1992).

Alverno et al, *Indicators of adverse somatic outcome in three Veterans Affairs nursing homes*, Hosp Community Psychiatry, vol. 43, pp. 1223–1226 (1992).

Goode et al, *Vitamin C depletion and pressure sores in elderly patients with femoral neck fracture*, BMJ (England), vol. 305, pp. 925–927 (1992).

Galgut et al, *A 4–year controlled clinical study into the use of a ceramic hydroxylapatite implant material for the treatment of periodontal bone defects*, J Clin Periodontal (Denmark), vol. 19, pp. 570–577 (1992).

Salim, *Sulphydryl–containing agents stimulate the healing of duodenal ulceration in man*, Pharmacology (Switzerland), vol. 45, pp. 170–180 (1992).

Bartold et al, *Platelet–derived growth factor reduces the inhibitory effects of lipopolysaccharide on gingival fibroblast proliferation*, J Periodontal Res, vol. 27, pp. 499–505 (1992).

Maitra et al, *Role of zinc in post–injury wound healing*, Arch Emerg Med, vol. 9, pp. 122–124 (1992).

Tudor et al, *Factors to focus on*, Nurs Times, vol. 88, pp. 62, 64, 66 (1992).

Verstraeten et al, *Effects of vitamin A on retinal pigment epithelial cells in vitro*, Invest Ophthalmol Vis Sci, vol. 33, pp. 2830–2838 (1992).

Miller, *The concept of the "Super Clot" is osseous grafting*, Compendium, vol. 13, pp. 236–242 (1992).

Scott et al, *Pressure ulcer development in the operating room*, Nursing implications, AORN J, vol. 56, pp. 242–250 (1992).

Bergstrom et al, *A prospective study of pressure sore risk among institutionalized elderly*, J Am Geriatr Soc, vol. 40, pp. 747–758 (1992).

Daly et al, *Enteral nutrition with supplemental arginine, RNA, and omega–3 fatty acids in patients after operation: immunologic, metabolic, and clinical outcome*, Surgery, vol. 112, pp. 56–67 (1992).

Dylewski, *Vitamin C supplementation in the patient with burns and renal failure*, J Burn Care Rehabil, vol. 13, pp. 378–380 (1992).

Smither et al, *Effects of platelet activating factor on endothelial cells and fibroblasts in vitro*, EXS, vol. 61, pp. 230–234 (1992).

Silane, *Systemic and other factors that affect wound healing*, Nurs RSA, vol. 7, pp. 41–46 (1992).

Fleming et al, *Effect of recombinant human growth hormone on catabolic hormones and free fatty acids following thermal injury*, J Trauma, vol. 32, pp. 698–702 (1992).

Starer et al, *Medical care of the elderly in the nursing home*, J Gen Intern Med, vol. 7, pp. 350–362 (1992).

Milner, *Acetic acid to treat Pseudomonas aeruginosa in superficial wounds and burns*, Lancet, vol. 340, p. 61 (1992).

Rittenberg et al, *Free fatty acids and dialyzed serum alternations of fibroblast populated collagen lattice contraction*, Tissue Cell, vol. 24, pp. 243–251 (1992).

Kang et al, *Uptake, distribution and fate of bacterial lipopolysaccharide in monocytes and macrophages: an ultrastructural and functional correlation*, Electron Microsc Rev, vol. 5, pp. 381–419 (1992).

Utley, *Nutritional factors associated with wound healing in the elderly*, Ostomy Wound Manage, vol. 38, pp. 22, 24, 26–27 (1992).

Cullum et al, *Intrinsic factors associated with pressure sores in elderly people*, J Adv Nurs, vol. 17, pp. 427–431 (1992).

Summerfield et al, *Morphologic findings in bone marrow precursor cells in zinc-induced copper def.*

Gongloff, *Alveolar ridge augmentation with collagen tubes containing bone and hydroxylapatite*, Int J Oral Maxillofac Surg, vol. 21, pp. 12–16 (1992).

Cornell et al, *Newest factors in fracture healing*, Clin Orthop, vol. 277 pp. 297–311 (1992).

Cook et al, *A randomized comparison of three post–tonsillectomy diets*, Clin Otolaryngol, vol. 17, pp. 28–31 (1992).

Abruzzese, *What causes pressure ulcers to heal?*, Decubitus, vol. 5, p. 6 (1992).

Griffin et al, *Efficacy of high voltage pulsed current for healing of pressure ulcers in patients with spinal cord injury*, Phys. Ther., vol. 71, pp. 433–444 (1991).

McClain et al, *Trace metals in liver diseases*, Semin. Liver Dis., vol. 11, pp. 321–339 (1991).

Billington, *Angiogenesis and its inhibition: Potential new therapies in oncology and non–neoplastic diseases*, Drug Des. Discov. (U.K.), vol. 8, pp. 3–35 (1991).

*Total parenteral nutrition in surgical patients*, Am. Fam. Phys., vol. 44, pp. 2210+2212 (1991).

Lipschitz, *Malnutrition in the elderly*, Semin. Dermatol., vol. 10, pp. 273–281 (1991).

Millikan, *Fibrel and wound healing*, Clin Dermatol, vol. 9, pp. 569–572 (1991).

Cynober, *Ornithine alpha–ketoglutarate in nutritional support*, Nutrition, vol. 7, pp. 313–322 (1991).

Malm et al, *Effect of low power gallium arsenide laser on healing of venous ulcers*, Scan J Plast Reconstr Surg Hand Surg, vol. 25, pp. 249–251 (1991).

LeVasseur et al, *A double–blind clinical trial to compare the efficacy of an active based cream F14001 against a placebo non–active based cream for the treatment of pressure ulcers in a population of elderly patients*, J Adv Nurs, vol. 16, pp. 952–956 (1991).

Wallace et al, *Energy balance studies and plasma catecholamine values for patients with healed burns*, J Burn Care Rehabil, vol. 12, pp. 505–509 (1991).

Burd et al, *Hyaluronan and wound healing: a new perspective*, Br J Plast Surg, vol. 44, pp. 579–584 (1991).

Torley et al, *A double blind, randomised, multicentre comparison of two doses of intravenous iloprost in the treatment of Raynaud's phenomenon secondary to connective tissue diseases*, Ann Rheum Dis, vol. 50, pp. 800–804 (1991).

Breslow et al, *Malnutrition in tubefed nursing home patients with pressure sores*, JPEN J Parenter Enteral Nutr, vol. 15, pp. 663–668 (1991).

Hosemann et al, *Normal wound healing of the paranasal sinuses: clinical and experimental investigations*, Eur Arch Otorhinolaryngol, vol. 248, pp. 390–394 (1991).

Farrar et al, *Milestones in clinical pharmacology. Wound healing*, Clin Ther, vol. 13, pp. 430–434 (1991).

Erlichman et al, *Common complications of wound healing. Prevention and Management*, Surg Clin North Am, vol. 71, pp. 1323–1351 (1991).

Hotz, *Aveolar ridge augmentation with hydroxylapatite using fibrin sealant for fixation. Part II: Clinical application*, Int J Oral Maxillofac Surg, vol. 20, pp. 208–213 (1991).

Konturek et al, *Epidermal growth factor in protection, repair, and healing of gastroduodenal mucosa*, J Gastroenterol, vol. 13, Suppl 1, pp. S88–97 (1991).

Arakawa et al, *H–2 receptor antagonist–refractory ulcer: its pathophysiology and treatment*, J Clin Gastroenterol, vol. 13 Suppl 1, pp. S129–133 (1991).

Faure et al, *Parenteral supplementation with zinc in surgical patients corrects postoperative serum–zinc drop*, Biol Trace Elem Res, vol. 30, pp. 37–45 (1991).

Motta, *The effectiveness of Dermagran topical therapy for treating chronic wounds in nursing facility residents*, Ostomy Wound Manage, vol. 36, pp. 35–38 (1991).

Rosen et al, *Porous block hydroxyapatite in orthognathic surgery*, Angle Orthod Fall, vol. 61, pp. 185–191 (1991).

Yukna, *Clinical comparison of hydroxyapatite–coated titanium dental implants placed in fresh extraction sockets and healed sites*, J Periodontal, vol. 62, pp. 468–472 (1991).

Ahmed et al, *A double–blind study of microprostol (SC–29333) in the healing of duodenal ulcer*, J Gastroenterol Hepatol, vol. 6, pp. 179–180 (1991).

Cummings, *Tissue viability. Managing the patient with fractured femur*, Nurs Stand Spec Suppl, No. 13, pp. 11–13 (1991).

Harju et al, *Clinical and metabolic effects and wound healing metabolism in controlled total parenteral nutrition with high vs. low nitrogen content for seven days after abdominoperineal rectum resection for carcinoma*, Chir Ital, vol. 42, pp. 151–164 (1990).

Ryan, *Wound healing and current dermatologic dressings*, Clin Dermatol, vol. 8, pp. 21–29 (1990).

ENTERAL FORMULATION DESIGNED FOR OPTIMIZED WOUND HEALING

BACKGROUND OF THE INVENTION

The present invention relates generally to nutritionally fortified pharmaceutical compositions and methods for providing nutrition. More specifically, the present invention relates to methods for providing nutrition to patients suffering from acute and/or chronic wounds.

Health care professionals involved in acute and long term care treatment constantly struggle with patients suffering from complications associated with delayed wound healing. Members of health care teams experience the increased demand in treatment time, labor, length of stay, cost, and patient suffering that results from delayed wound healing. Providing adequate nutrition to patients suffering from delayed wound healing is a necessary step of the healing process. Appropriate nutritional support not only affects the patient's ability to resist tissue breakdown, but can help to defray the financial burden associated with impaired wound healing. For instance, the enormous cost of treating lingering pressure ulcers significantly affects the financial burden of institutions and healthcare payment systems.

Irrespective of the particular type of wound, acute and chronic (long term care) wound patients collectively experience delayed wound healing. Many clinical situations in acute and long term care settings, such as surgery, trauma, burns, diabetes, pressure ulcers and vascular ulcers, are associated with a high instance of impaired wound healing. For instance, diabetic patients and those on systemic steroids often have impaired healing mechanisms affecting their ability to resist tissue breakdown. Still further, patients suffering from pressure or decubitus ulcers or inflicted with surface or shallow wounds often experience delayed healing.

Treating patients suffering from such delayed wound healing is a complicated process. The pathophysiology of wound healing is complex and multifactorial. Current concepts suggest that healing involves the following mechanisms: (1) inflammation; (2) fibroblast proliferations, collagen synthesis; (3) angiogenesis; (4) wound contracture; and (5) epithelialization. See, for example, Roberts, *Nutrition and Wound Healing*, Nutrition in Critical Care, (Zaloga GP ed.) Mosby, St. Louis, pp. 525–544 (1994); and Cohen et al, *Wound Healing-Biochemical and Clinical Aspects*, (Lindblad WJ eds.), WB Saunders, Philadelphia, pp. 1–630 (1992). Numerous factors, including metabolic factors, immune function, cytokines, eicosanoids, free radical production, and nutrient availability, affect these mechanisms.

As a result, the success of wound healing is dependent on many interrelated factors. Aside from the need for direct wound care, one of the most important factors in treating wound healing is providing adequate nutrition and avoiding malnutrition. It is well recognized that malnutrition can delay the healing process. In fact, a wound may simply not heal if adequate nutrition is not provided throughout the healing process. Wound healing depends, in part, on adequate nutrition provided by a well balanced diet of protein, carbohydrate, fat, vitamins, minerals, trace elements, and water.

Acute or chronic wound patients often exhibit increased nutritional requirements. For example, patients suffering from chronic post-surgical wounds, impaired-healing burns and decubitus ulcers have a significant need for increased nutrients and energy as compared to individuals who are not challenged by such metabolic stresses. Indeed, non-essential nutrients and substances that a body typically can synthesize in adequate supply may become limiting. Moreover, providing the necessary nutritional support to such patients helps meet the protein, energy, vitamin, and mineral requirements necessary to optimize healing of such patients.

Numerous enteral products have been targeted for wound healing. These products include: REPLETE®, PEPTAMEN® VHP, CRUCIAL™, IMPACT®, ALITRAQ®, IMMUN-AID®, PERATIVE™ and TRAUMACAL®. Although such products are used in an attempt to treat and/or provide nutritional requirements for patients with wounds, the inventors of the present invention do not believe that these products adequately meet the needs of patients with acute or chronic wounds. Current products either lack adequate proline or do not even address the specific needs of such patients.

Therefore, a need exists for a nutritional formulation that specifically addresses the nutrient requirements of patients in the acute or long term care setting.

SUMMARY OF THE INVENTION

The present invention provides a nutritional formulation that meets the nutrient requirements of acute and chronic wound patients. The present invention meets the unique nutrient needs of the acute and chronic wound-healing patient that are generated due to tissue repair and healing requirements.

To this end, in an embodiment, the present invention provides a method for providing nutritional support to patients with an acute or chronic wound comprising the step of administering a therapeutically effective amount of a composition. The composition includes a unique protein profile. The protein source includes an arginine source in an amount of at least 2% of the total calories of the composition and a proline source in an amount of at least 2% of the total calories of the composition.

In an embodiment, the protein source is approximately 18% to about 35% of the total calories of the composition.

In another embodiment, a method for promoting optimal collagen synthesis in a patient suffering from an acute or chronic wound is provided comprising administering a therapeutically effective amount of a composition with an improved protein source. The protein source contains an arginine source and a proline source in a ratio by weight of approximately 1:0.5 to about 4:1.

Moreover, in an embodiment, a method for providing nutritional support to a patient is provided wherein the arginine source is in an amount of at least approximately 3.0% of the total calories of the composition.

In an embodiment, a method for providing nutritional support to a patient is provided wherein the proline source is in an amount of at least approximately 3.0% of the total calories of the composition.

In yet another embodiment, the arginine source is approximately 2% to about 6% of the total calories of the composition.

In another embodiment, the proline source is approximately 2% to about 4% of the total calories of the composition.

Still further, in an embodiment, the composition of the present invention includes a carbohydrate and lipid source.

In an embodiment, the composition has a caloric density of about 1.0 kcal/ml.

The present invention also provides a method for providing nutritional support to a patient with delayed wound healing due to an acute or chronic wound comprising the step of enterally administering a therapeutically effective amount of a composition. The composition includes a protein source having an arginine component and a proline component. The arginine component and the proline component are present in a ratio by weight of approximately 1:0.5 to about 3:1.

In an embodiment, the composition includes a lipid source and a carbohydrate source.

In still another embodiment, the proline source is in an amount of approximately 5 to about 10 g/1000 kcal and the arginine source is in an amount of approximately 5 to about 15 g/1000 kcal.

An advantage of the present invention is that it minimizes complications in post-surgical patients.

Moreover, an advantage of the present invention is that it reduces the financial burden to institutions and health care systems as a result of less wound care time, decreased complications and possibly less rehospitalizations.

Another advantage of the present invention is that the composition is a ready-to-use product that does not need to be mixed with water, thus decreasing the chance of bacterial contamination during the mixing process.

A further advantage of the present invention is that it provides more than the U.S. RDAs for vitamin A, vitamin C, beta-carotene, vitamin E, thiamin, pyridoxine, biotin and zinc in 1000 kcal of the composition. An increase in these various nutrients further optimizes wound healing.

Another advantage of the present invention is that it improves collagen synthesis/deposition. This in turn contributes to better wound repair.

Still further, an advantage of the present invention is that it meets the U.S. RDA's in 1000 kcal.

Moreover, an advantage of the present invention is that it provides a composition having a high protein content, a high lipid content and a caloric density that meets the increased protein and energy needs of patients with acute or chronic wounds.

Another advantage of the present invention is that it provides an enteral nutritional formulation that is designed to optimize nutrient absorption and wound healing in patients with decubitus ulcers.

Yet another advantage of the present invention is that it may decrease the morbidity rate for geriatric patients with decubitus ulcers.

Moreover, an advantage of the present invention is that it provides a combination of proline and arginine in conjunction with adequate protein, an appropriate n6:n3 ratio, and higher than typical levels of key vitamins and minerals to promote collagen synthesis and wound healing.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides nutritional compositions and methods for the treatment of a patient population benefiting from a product with demonstrable efficacy in the promotion of collagen synthesis and wound healing. The nutritional composition contains a unique protein profile containing both arginine and proline.

With respect to the treatment aspect, the present invention can be utilized to treat acute and/or chronic wound healing patients. Among others, such patients include, for example, Type I diabetics with necrotizing fasciitis, nursing home patients with decubitus ulcers, hospitalized and homecare post-surgical patients with acute or chronic wounds, long-term tube fed patients suffering from a wound, and subacute care patients suffering from a wound. Specifically, the present invention provides methods for providing nutritional support for wound healing patients in an acute or long term care setting.

Pursuant to the present invention, a formulation is provided that is designed to optimize collagen synthesis and wound healing in patients with acute and chronic wounds. The formulation of the present invention meets the nutrient requirements unique to acute and chronic wounds. The formulation can be provided as an enteral product, as a parenteral product (i.e. through intravenous solutions) or can be incorporated in various solid food products.

In a preferred embodiment, pursuant to the present invention, a ready-to-use enteral formula is provided. The formulation can provide the total nutritional requirements of the long-term tube fed or acute care patient. The formulation can also act as an oral supplement. The product, however, is preferably designed to be fed to the patient by tube. This product can be provided, for example, in cans or by a spike and hang bag system. The product is ready to use and does not require reconstitution or mixing prior to use.

An important phase of wound healing is the formulation of granulation tissue, which is primarily composed of proteins. For instance, to heal decubitus ulcers, patients require increased protein intake. Adequate protein intake is a critical component of fibroblast formation, collagen synthesis, wound contraction, and scar formation. Protein is also important for the formation of antibodies and leukocytes needed to prevent wound infection.

The inventors have surprisingly discovered that two amino acids, arginine and proline, in combination, resulted in a significant improvement in the parameters used to gauge wound healing. These parameters include at least fresh breaking strength and collagen synthesis.

Although neither arginine nor proline are considered to be essential dietary amino acids, it is proposed that the body's ability to synthesize these amino acids may not be adequate after acute or chronic wounds, even if the dietary protein provided is sufficient. It is also proposed that the "nonessential" amino acids, such as arginine and proline, become "conditionally essential" under various conditions. Under certain metabolic, developmental and pathophysiologic conditions, one or more of the nonessential amino acids may limit the conservation and deposition of body protein. Therefore, the formulation of the present invention has been supplemented with additional arginine and proline in quantities sufficient to promote optimal collagen synthesis in acute or chronic wounds and thus, optimizes wound healing. The present invention preferably provides a ratio by weight of arginine to proline ranging from approximately 1:0.5 to about 4:1.

The protein source of the present invention includes approximately 18% to about 35% of the total calories. In an embodiment, the protein source comprises 25%, by calories, of the composition. In this regard, the protein concentration is preferably 62.5 g/1000 kcal and 90 g/day, assuming a 1500 kcal intake is provided.

Pursuant to the present invention, the protein source includes intact or hydrolyzed proteins (i.e. peptides produced by protein degradation) supplemented with free amino acids. A variety of different protein sources can be utilized pursuant to the present invention. For example, suitable intact protein sources include soy, whey, casein or blends of same. In an embodiment, the protein source is selected from either a soy:whey or casein:whey blend. Preferably, these protein blends of the present invention are selected to yield the highest amounts of arginine and proline in the proteins so that a minimal amount would be needed in the form of free amino acids. In an embodiment, the protein source includes casein.

Alternatively, the protein source can be a hydrolyzed protein. Such peptide based diets promote improved growth rates and wound healing. A variety of hydrolyzed proteins can be utilized in the present invention. Suitable examples include casein hydrolysate and whey hydrolysate.

Pursuant to the present invention, this formulation has a high arginine content. This high arginine content, in the formulation of the present invention, includes arginine in the protein sources plus arginine added as free amino acids or as arginine-rich peptides. The composition includes from approximately 2.0% to 6.0% (10–30 g/day, assuming a 2000 kcal daily intake; 5.0–15.0 g/1000 kcal), by calories, as arginine. Preferably, at least approximately 4% to about 5% of the total calories of the composition are provided as arginine. This range provides approximately 10 to 12.5 g/1000 kcal. This is above the ad libitum intake of arginine in a typical United States diet, which is approximately 0.8% of calories or, e.g., 4 g/day, assuming a 2000 kcal daily intake. In an embodiment of the present invention, the formulation includes approximately at least 4% of the total calories as arginine.

In conjunction with arginine, the formulation also has a high proline content. Preferably, approximately 2% to about 4% of the total calories of the composition are provided as proline. This range provides approximately 5.0–10.0 g proline/1000 kcal and 10–20 g/day, assuming a 2000 daily kcal intake. This is above the ad libitum intake of proline in the typical United States diet, which is approximately 1.8% of total calories or, e.g., 9 g/day, assuming a 2000 kcal intake (4.5 g/1000 kcal). In an embodiment, the proline content is at least approximately 3% of the total calories.

Similar to the arginine content, proline in the formulation of the present invention includes proline in intact protein sources plus proline added as free amino acids or as proline-rich peptides.

The total calories/nitrogen in the composition of the present invention is approximately 91:1. The total non-protein calories/grams of nitrogen is approximately 68:1.

The formulation of the present invention also includes a lipid fraction. Lipids or fats are the primary source of stored energy. Energy from fat metabolism is used in all normal cell functions. Fat metabolism results in the formation of prostaglandins and other regulators of the immune and inflammatory process. Fat is an essential component of intracellular organelles and is an integral component of cell membranes.

Preferably, the present invention includes approximately 20% to 45%, by calories, as lipids. In an embodiment, approximately 30% of the formulation, by calories, is provided as lipids.

The lipid fraction of the present invention contains significant amounts of omega-6 rich fatty acids and medium chain triglycerides (MCTs). Preferably, the lipid fraction comprises approximately 20% to 70% by weight MCTs. In a preferred embodiment, the lipid fraction includes approximately 50% by weight MCTs. MCTs are more easily absorbed and metabolized as compared to long chain triglycerides. The use of MCTs will reduce the risk of the potential for nutrient malabsorption.

In an embodiment, approximately 50% of the lipid component is MCTs; 30% is canola oil; 10% is corn oil; 6% is soy lecithin; and 4% is milk fat. This will provide an omega-6:omega-3 ratio of approximately 5:1.

Still further, the present invention includes a carbohydrate source. Carbohydrates, and more particularly glucose, is the primary fuel for cellular metabolism of many tissues, including leukocytes, fibroblasts and macrophages. Glucose is needed, therefore, to meet the metabolic demand for wound healing and preserve the body's structural and functional protein. When glucose is not available for cellular function, the body catabolizes protein, and to a lesser degree fat, to produce glucose to meet energy requirements.

Carbohydrates are present in the composition in an amount of approximately 25% to 65% of the total calories. Preferably, in an embodiment, the carbohydrates comprise 45% of the total calories. This is equivalent to 113 g/liter. Suitable sources, among others, of carbohydrates include maltodextrin, cornstarch, sucrose and corn syrup solids.

In addition to the ability of the proper ratio of omega-6 to omega-3 fatty acids to modulate immune function, antioxidant vitamins and minerals also reduce the incidence of severe inflammatory reactions. Vitamins, minerals and trace elements are necessary for cellular metabolism and are critical for wound healing. Increased metabolism frequently occurs in the wound healing patient. The natural process of wound healing requires numerous energy consuming reactions. These energy-consuming reactions all require increased amounts of vitamins, minerals and trace elements.

Preferably, anti-oxidant vitamins and minerals are increased to above the U.S. RDAs. This will ensure that the patient receives at least 100% of the U.S. RDA as well as insure that any additional micronutrients that are necessary, due to the patient's state, will be provided.

The formulation, in a embodiment, will provide approximately 2–5 mg/1000 kcal of beta-carotene. Beta-carotene is a precursor for vitamin A and has some unique antioxidant properties. The formulation further provides, per 1000 kcal, approximately 3000–5000 I.U. of vitamin A; approximately 400–1000 mg vitamin C; approximately 48–80 I.U. vitamin E; approximately 2–4 mg thiamine; approximately 3–5 mg pyridoxine; approximately 0.4–0.6 mg biotin; and approximately 20–30 mg zinc.

Of course, it will be appreciated that a variety of formulations are possible in accordance with the present invention. An example of a formulation in accordance with the present invention includes a formulation having a caloric density of 1.0 kcal/ml. This is equivalent to 250 kcal/250 ml which will be one unit (can or container) of product.

By way of example, and not limitation, examples of the present invention will now be given.

FORMULA EXAMPLE NO. 1

A liquid, ready-to-use enteral product with protein at 25% of total calories in the formula: 2.0 to 6.0% from arginine and 2.0 to 4.0% from proline. A suitable protein source is casein plus L-proline and L-arginine. Carbohydrates comprise 45% of calories. Lipids comprise 30% of calories. The lipids may be a blend of medium chain triglycerides (50% by weight), canola oil (30% by weight), corn oil (10% by weight), soy lecithin (6% by weight) and milk fat (4% by weight). Vitamin and mineral content preferably meets United States daily requirements in 1000 calories with higher than the U.S. RDA levels of important vitamins and minerals for normal healing such as vitamin A, beta-carotene, vitamin C, vitamin E, thiamine, pyridoxine, biotin and zinc.

FORMULA EXAMPLE NO. 2

A liquid ready-to-use enteral product made pursuant to the present invention may have the following nutrient profile:

| Nutrient Composition | Per 250 ML |
|---|---|
| Protein (g) | 15.625 |
| Carbohydrate (g) | 28.175 |
| Fat (g) | 8.65 |
| Vitamin A (IU) | 1000 |
| Beta-Carotene (mg) | 0.5 |
| Vitamin D (IU) | 100 |
| Vitamin E (IU) | 15 |
| Thiamin (mg) | 0.75 |
| Pyridoxine (mg) | 1.0 |
| Biotin (mcg) | 100 |
| Zinc (mg) | 6 |
| Copper (mg) | 0.5 |
| Magnesium (mg) | 100 |
| Selenium (mcg) | 25 |
| Sodium (mg) | 219 |
| Potassium (mg) | 375 |
| Chloride (mg) | 325 |

A liquid ready-to-use enteral product made pursuant to the present invention may have the following nutrient profile:

FORMULA EXAMPLE NO. 3

| Caloric Density | 1.0 kcal/ml |
|---|---|
| Protein | 25% kcal (62.5 g/L) |
| Caseinate | 82.5% kcal |
| Free amino acid arginine | 13.3% kcal |
| Free amino acid proline | 4.2% kcal |
| Total Arginine | 10.0 g/L |
| Total Proline | 7.5 g/L |
| Total Cysteine | 0.2 g/L |
| Total Glutamine | 4.6 g/L |
| Carbohydrate | 45% kcal (112.7 g/L) |
| Corn Syrup Solids | 62% kcal |
| Sucrose | 38% kcal |
| Fat | 30% kcal (34.6 g/L) |
| % By Weight | |
| Corn Oil | 14% by wt. |
| Canola Oil | 30% by wt. |
| MCT (Coconut Oil) | 50% by wt. |
| Soy Lecithin | 6% by wt. |
| Residual Milk Fat | <1% by wt. |
| N6:N3 Ratio | 5:1 |
| Osmolality | 530 mosm (estimated) |
| Density | 1.960 g/ml |
| Water | 840 ml/l (84%) |
| CAL/gN ratio | 91:1 |
| NPC/gN ratio | 68:1 |

Legend
*Total sucrose includes what is added as sucrose plus the sucrose content of the vanilla flavoring agents added to the composition.

By way of example, and not limitation, experimental examples detailing the use of the present invention will now be given.

EXPERIMENTAL EXAMPLE NO. 1

Male adult Sprague-Dawley rats were obtained from a commercial breeder (Harlan Sprague/Dawley, Indianapolis, Ind.). Rats were housed individually in stainless steel cages at a constant temperature (25°±1° C.) and relative humidity (40–50%). The cages were kept in a room with a 12 hr light—12 hr dark cycle. All animals were allowed at least one week of acclimatization to the laboratory conditions prior to use in the experiments. During this time, they were fed a standard laboratory chow in powder form containing 1.69% arginine (Teklad 4% Mouse/Rat Diet 7001, Harlan Teklad, Madison, Wis.) and drank tap water ad libitum.

After the period of acclimatization, when the rats weighed between 290–326 g, they were randomly placed into four groups. Under pentobarbital anesthesia, they were weighed, their backs were shaved and scrubbed with an organic iodine solution and a seven centimeter dorsal skin incision was made down to the level of the panniculus carnosus. At the cephalad portion of the wound two subcutaneous pockets were made into which sterile, preweighed, saline moistened PVA sponges were inserted. The wound was closed with seven skin staples. The rats tolerated the procedure well and recovered uneventfully.

The four groups received the following amino acid supplementations (all from Sigma Chemical Co., St. Louis, Mo.):

1. 0.65% glycine and 0.65% alanine.
2. 1.0% arginine HCl.
3. 0.5% proline.
4. 1.0% arginine HCl and 0.5% proline.

All amounts are w/w basis and were chosen to provide equal amount of amino acid, not isonitrogenous amounts.

Half the amino acid supplement was added to the aforementioned chow diet and half was added to the drinking water. To alleviate any taste differences from the free amino acids in solution, Sweet and Low was added to all drinking solutions (one pack/L). The powdered diet and the water were given ad libitum. The rats were weighed and their water intake was measured daily.

On the tenth day post-wounding, rats were sacrificed with an overdose of pentobarbital. Before cardiac function ceased, blood was obtained by cardiac puncture and aliquoted for total protein and albumin determinations. Serum was collected from the remainder and frozen at −20° C. for possible future serum amino acid determinations. The pelt containing the healing scar was excised. The PVA sponges were removed, carefully cleared of surrounding tissue and frozen at −20° C. for subsequent determination of hydroxyproline content as an index of wound reparative collagen accumulation using the method of Woessner. See J. Woessner, *Determination of Hydroxyproline in Tissue and Protein Samples Containing Small Proportions of this Amino Acid*, Biochem. Biophys, Vol. 93, p. 440 (1961). The pelt was cut on a multibladed guillotine into seven equal strips (0.7 cm×6 cm), each strip centered by a segment of the healing scar. Fresh breaking strengths were measured on strips 1, 3, 5 and 7 (cephalad to caudal) using a constant speed tensiometer (available from W. C. Dillon & Co., Inc., Van Nuys, Calif.). Strips 2, 4 and 6 were kept for at least 72 hr in 10% formalin (to maximally crosslink the collagen) for determination of fixed breaking strengths.

RESULTS

Tables 1 and 2 below set forth results for the nutritional and wound healing parameters, respectively, that were evaluated in the experiment. All data are reported as mean ±SEM. Statistical analysis was carried out using the StaView Program on a Macintosh Computer and applying analysis of variance (ANOVA) with Scheffe's F-test being applied for post hoc analysis. In Tables 1 and 2, the following abbreviations are utilized: Ala=alanine; Gly=glycine; Arg=arginine; and Pro=proline.

TABLE 1

Nutritional Parameters

| Group | Beginning BW (g) | End BW (g) | Total Protein (g/dL) | Albumin (g/dL) |
|---|---|---|---|---|
| Ala/Gly (1) | 302.7 ± 2.4 | 328.0 ± 4.0 | 5.4 ± 0.11 | 3.1 ± 0.08 |
| ARG (2) | 304.7 ± 3.6 | 325.0 ± 3.1 | 5.5 ± 0.13 | 3.2 ± 0.1 |
| PRO (3) | 311.1 ± 2.1 | 333.6 ± 4.2 | 5.2 ± 0.06 | 2.9 ± 0.05 |
| Arg/Pro (4) | 311.8 ± 2.9 | 339.4 ± 3.4 | 5.3 ± 0.09 | 3.0 ± 0.05 |

TABLE 2

Wound Healing Data

| Group | FRESH BS (g) | FIXED BS (g) | OHP (mg/100 mg sponge weight) |
|---|---|---|---|
| Ala/Gly (1) | 283 ± 9$^{a,b}$ | 1257 ± 51$^{a,b}$ | 1172 ± 80$^{a,b}$ |
| ARG (2) | 395 ± 13$^{b,c}$ | 1453 ± 27$^c$ | 1526 ± 50$^c$ |
| PRO (3) | 279 ± 15$^b$ | 1152 ± 43 | 1169 ± 88 |
| Arg/Pro (4) | 453 ± 12$^c$ | 1568 ± 46$^c$ | 1846 ± 111$^c$ |

Legend
$^a$p < 0.001 vs arginine
$^b$p < 0.001 vs arg/pro
$^c$p < 0.001 vs proline
BS = breaking strength
OHP = collagen synthesis
BW = body weight

CONCLUSIONS

The data illustrate that all animals gained weight equally well in the post-op period. In addition, no differences in the amount of drinking water were noted so intake of the amino acid supplements can be assumed to have been equal in all groups. No statistical differences were noted in the plasma nutritional parameters. Amino acid levels in plasma were not measured.

Most notably, the wound healing studies revealed:

1. Arginine supplementation enhanced wound breaking strength and collagen accumulation when compared to either the glycine/alanine group (control) or the proline group.

2. Addition of proline to arginine supplementation (ARG/PRO group) resulted in significant enhancement in wound fresh breaking strength and an over 20% increase in wound collagen deposition, which however failed to achieve statistical significance by ANOVA.

Rats fed a supplement of arginine and proline after wound infliction resulted in a higher breaking strength and an increase in deposition of hydroxyproline (a measure of collagen synthesis) than when fed proline alone.

The interpretation of these data would suggest that arginine and proline have a synergistic effect in enhancing wound healing. Although the exact mechanism of action remains to be elucidated, addition of proline to the arginine, in a specific ratio resulted in: 1) a significant enhancement in wound fresh breaking strength; and 2) over a 20% increase in wound collagen deposition.

EXPERIMENTAL EXAMPLE NO. 2

The inventors conducted an additional experiment to demonstrate the efficacy of the combination arginine and proline compared with a diet containing only supplemental arginine or a diet containing arginine and a combination of glycine and alanine. Notably, glycine and alanine were used in the present experiment as a control in order to match total nitrogen intake. Another objective of the present experiment was to establish the dose-response effect of proline on wound breaking strength and collagen deposition against a constant background intake of arginine and constant nitrogen intake. In this regard, the inventors performed this experiment to determine the most effective dose of proline when given with arginine.

Fifty male Sprague Dawley rates, weighing approximately 250 to 300 grams, underwent a standardized midline dorsal wound. Under general anesthesia achieved by intraperitoneal pentobarbital injection (3.5 mg/100 mg body weight), the rats had their backs shaved with electric clippers and prepped with povidone iodine (Betadine) solution. The entire technique was performed under aseptic conditions. A seven centimeter midline dorsal skin incision, down to the level of the panniculus carnosum, was created using a scalpel with a #15 blade and a wound director. Two equally sized subcutaneous pockets were placed on each side of the cephalad end of the wound. A preweighed, sterile, and saline moistened polyvinyl alcohol sponge (Unipoint Industries, Inc., North Point, N.C.) was placed into each of these pockets. The skin was closed with six equally spaced surgical staples.

Postoperatively, the animals were divided into five groups of ten and each group was fed a powdered commercial laboratory chow (Teklad 4% Mouse-Rat Diet 7001, Harlan Tekblad, Madison Wis.) and supplemented as indicated on Table 3.

TABLE 3

| Group | Arginine (g/100 g) | Proline (g/100 g) | Glycine (g/100 g) | Alanine (g/100 g) |
|---|---|---|---|---|
| 1 | 1.0 | 0 | 0 | 0 |
| 2 | 1.0 | 0 | 0.65 | 0.77 |
| 3 | 1.0 | 0.500 | 0.490 | 0.583 |
| 4 | 1.0 | 1.0 | 0.327 | 0.388 |
| 5 | 1.0 | 2.0 | 0 | 0 |

All amino acid supplements were incorporated into the chow diet. The chow diet, prior to the addition of the amino acids supplements, contained 1.7% arginine and 1.5% proline. Food intake and body weights were monitored daily. After ten days, the animals were sacrificed with a lethal dose of intraperitoneal pentobarbital. The skin staples were removed. The dorsal pelt containing the healing scar was excised down to the level of the panniculus carnosum with complete preservation and incorporation of the wound in the specimen. The two sponges were harvested, cleared of surrounding granulation tissue, sealed in aluminum foil and stored at −20° C. for subsequent hydroxyproline (OHP) assay using the method of Woessner.

Wound breaking strength was determined for both fresh and fixed specimens (WBS-Fresh and WBS-Fixed) using a constant speed tensiometer (available from WC Dillon and Co., Van Nuys, Calif.). Each wound was cut into seven equal 0.7 cm width strips using a multiblade guillotine. Strips were numbered from cephalad to caudad. Strips 1, 3, and 6 were used for fresh breaking strength determination and strips 2, 5 and 7 were soaked in 10% formalin for 72 hours prior to breaking strength determination. Collagen synthesis (OHP), serum urea nitrogen (SUN), creatine, albumin, and total protein were also measured.

RESULTS

The results of the experimental study are outlined below in Table 4. In Table 4, the values are expressed as the mean plus or minus the standard deviation. The following abbreviations are utilized: Arg=arginine; Pro=proline; Ala=alanine; and Gly=glycine. The stats equal 1 factor ANOVA with contrasts examined using Fischer PLC.

TABLE 4

| | Treatment Control Number | | | | |
|---|---|---|---|---|---|
| | 1 | 2 | 3 | 4 | 5 |
| Parameter | Arg Alone | Arg + Ala + Gly | Arg + 0.5% Pro + Ala + Gly | Arg + 1% Pro + Ala + Gly | Arg + 2% Pro |
| OHP | 1329.6 ± 364.4 | 1472.0 ± 325.6 | 1575.3 ± 194.1 | 1776.1 ± 317.5 | 1573.1 ± 353.7 |
| WBS-Fresh | 285.5 ± 67.1 | 372.8 ± 45.5 | 347.0 ± 60.9 | 388.3 ± 68.5 | 331.7 ± 38.7 |
| WBS-Fixed | 1274.4 ± 197.9 | 1514.3 ± 136.9 | 1416.7 ± 215.2 | 1383.4 ± 224.1 | 1422.8 ± 210.1 |
| SUN | 19.5 ± 3.6 | 21.2 ± 3.3 | 20.5 ± 2.1 | 20.3 ± 3.1 | 19.2 ± 2.3 |
| CREATINE | 0.6 ± 0.1 | 0.6 ± 0.2 | 0.5 ± 0.1 | 0.6 ± 0.2 | 0.6 ± 0.1 |
| ALBUMIN | 3.2 ± 0.7 | 3.1 ± 0.3 | 3.1 ± 0.3 | 3.0 ± 0.3 | 3.2 ± 0.4 |
| Total Protein | 5.5 ± 0.9 | 5.3 ± 0.4 | 5.4 ± 0.4 | 5.4 ± 0.4 | 5.5 ± 0.5 |
| Weight Gain | 9.5 ± 3.0 | 7.4 ± 3.3 | 8.5 ± 5.1 | 8.3 ± 3.4 | 7.5 ± 2.7 |
| Food Intake | 26.85 ± 1.15 | 26.23 ± 2.36 | 27.43 ± 1.56 | 26.06 ± 1.43 | 27.84 ± 1.64 |

With respect to the collagen synthesis (OHP) parameter, the following results were obtained. OHP values were significantly higher in Group 4 compared to Group 1. Group 4 OHP values were also significantly higher than Group 2 which received an equivalent nitrogen load. No proline dose response effect was observed. Group 2 was not different from Group 3 and Group 5. These groups were matched for total nitrogen intake but differed in the types of supplemental amino acids. Lastly, Group 1 was not different from Groups 3 and 5 which received the lowest and highest doses of proline, respectively.

With respect to the fresh breaking strength (WBS-Fresh) parameter, the following results were observed. Group 1 showed significantly lower values compared to Group 2, Group 3 and Group 4. Group 4 was significantly higher than Group 5. Groups 2, 3 and 4 performed similarly; these groups had equivalent nitrogen intakes but differed in the type of supplemental amino acids included in the diet.

With respect to the fixed breaking strength parameter (WBS-fixed), the following results were observed. Group 1 value was significantly lower than Group 2. Group 1 was not different from the three Groups (3-5) supplemented with proline. Groups 2-5, matched for nitrogen intake but differing in the type of amino acid supplemented, performed similarly.

In addition to the OHP, fresh breaking strength and fixed breaking strength parameters, other parameters were also studied. No significant treatment group differences were identified in SUN, Creatine, Albumin, total protein, % weight gain, or food intake.

CONCLUSIONS

This experiment demonstrated that select dietary treatments influenced wound healing. Specifically, consumption of a diet supplemented with arginine plus 1% proline significantly increased OHP synthesis compared to those groups consuming either a diet containing only supplemental arginine or a regimen containing arginine plus glycine plus alanine. The experiment also demonstrated that collagen synthesis was most improved in the treatment group receiving arginine plus 1% proline.

The experiment also showed improved fresh breaking strength values for the present invention. The group receiving arginine plus 1% proline outperformed the arginine alone group and the arginine plus 2% proline group in its effects on fresh breaking strength. Under the conditions of this experiment, fresh breaking strength was improved by increasing nitrogen intake independent of the source; fixed breaking strength was similar in all treatment groups. In contrast to the OHP results, the arginine plus 1% proline group did not outperform the isonitrogenous arginine plus glycine plus alanine group, which suggests that the effects may be linked to nitrogen intake. Notably, while the experiment demonstrated that a specific dose of proline was more effective than others, this is only an indication of what dose is effective under other experimental or clinical conditions. Hence, varying the proline range outside of this preferred dose naturally falls within the scope of the claimed invention.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for providing nutritional support to a patient with an acute or chronic wound comprising the step of administering a therapeutically effective amount of a composition comprising:

a protein source comprising an arginine source in an amount of at least 2% of the total calories in the composition and a proline source in an amount of at least 2% of the total calories in the composition;

a lipid source; and a carbohydrate source.

2. The method of claim 1 wherein the protein source comprises approximately 18% to about 35% of the total calories of the composition.

3. The method of claim 1 wherein the arginine source and the proline source are present in a ratio by weight of approximately 1:0.5 to about 4:1.

4. The method of claim 1 wherein the arginine source is present in an amount of at least 3.0% of the total calories of the composition.

5. The method of claim 1 wherein the proline source is present in an amount of at least 3.0% of the total calories of the composition.

6. The method of claim 1 wherein the arginine source comprises approximately 2.0% to about 6.0% of the total calories in the composition.

7. The method of claim 1 wherein the proline source comprises approximately 2.0% to about 4.0% of the total calories in the composition.

8. A method for promoting optimal collagen synthesis in acute or chronic wound patients comprising administering to the patient a composition having a protein source comprising a therapeutically effective amount of an arginine source and a proline source, the arginine source and proline source present in a ratio by weight of approximately 1:0.5 to about 4:1.

9. The method of claim 8 wherein the composition further comprises at least 100% of the U.S. RDA for vitamin A, vitamin C, beta-carotene, vitamin E, thiamin, pyridoxine, biotin and zinc.

10. The method of claim 8 wherein the arginine source comprises approximately 2.0% to about 6.0% of the total calories in the composition.

11. The method of claim 8 wherein the proline source comprises approximately 2.0% to about 4.0% of the total calories of the composition.

12. The method of claim 8 wherein the protein source comprises approximately 18% to about 35% of the total calories of the composition.

13. The method of claim 8 wherein the composition has a caloric density ranging from about 1.0 to 1.5 kcal/ml.

14. The method of claim 8 wherein the composition further comprises a lipid source and a carbohydrate source.

15. The method of claim 14 wherein the lipid source comprises a source of medium chain triglycerides, a source of omega-3 fatty acids and a source of omega-6 fatty acids.

16. The method of claim 14 wherein the lipid source comprises an omega-6 fatty acid to an omega-3 fatty acid ratio of approximately 5:1.

17. A method for providing nutritional support to an acute or chronic wound patient with delayed wound healing comprising the step of administering a therapeutically effective amount of a composition comprising:

a protein source including an arginine source and a proline source, the arginine source and the proline source present in a ratio by weight of approximately 1:0.5 to about 4:1.

18. The method of claim 17 wherein the proline source is in an amount of approximately 5.0 to about 10.0 g/1000 kcal of the composition and the arginine source is in an amount of approximately 5.0 to about 15.0 g/1000 kcal of the composition.

19. The method of claim 17 wherein the composition is administered enterally.

20. The method of claim 17 wherein the composition is administered parenterally.

* * * * *